United States Patent

Linder et al.

[11] Patent Number: 5,629,437
[45] Date of Patent: May 13, 1997

[54] PREPARATION AND USE OF ALKYLENEOXYSILANE COMPOSITIONS

[75] Inventors: Loren Linder, Warminster; Joel Zazyczny, Collegeville, both of Pa.

[73] Assignee: Huls America Inc., Somerset, N.J.

[21] Appl. No.: 593,611

[22] Filed: Jan. 30, 1996

[51] Int. Cl.$^6$ .................... C07F 7/08; C07F 7/18
[52] U.S. Cl. .......... 556/444; 556/445; 556/438; 556/439; 556/466; 556/482; 556/429; 549/215
[58] Field of Search .................. 556/444, 445, 556/438, 439, 466, 482, 429; 549/215

[56] References Cited

U.S. PATENT DOCUMENTS

| | | | |
|---|---|---|---|
| 3,887,602 | 6/1975 | Thum et al. | 556/445 |
| 4,839,443 | 6/1989 | Akutsu et al. | 556/445 X |
| 4,847,160 | 7/1989 | Munz et al. | 428/447 |
| 4,847,398 | 7/1989 | Mehta et al. | 556/445 |
| 5,051,129 | 9/1991 | Cuthbert et al. | 106/2 |
| 5,488,124 | 1/1996 | Cobb et al. | 556/445 |
| 5,492,994 | 2/1996 | Gentle et al. | 556/444 X |
| 5,527,933 | 6/1996 | Boutevin et al. | 556/445 X |

*Primary Examiner*—Paul F. Shaver
*Attorney, Agent, or Firm*—Abelman, Frayne & Schwab

[57] ABSTRACT

The invention is directed to water soluble silane compositions that are essentially alcohol free comprising compounds of the structure:

$$(RO)_{3-x}(HO)_x Si(CH_2)_3 (OCH_2 CH_2)_b OH \quad (Ia)$$

$$\{(RO)_{2-y}(HO)_y Si(CH_2)_3 (OCH_2 CH_2)_b O\}_z \quad (IIa)$$

wherein x ranges from 1 to 3, b ranges from 1 to 30, y is 0 or 1, and z ranges from 1 to 3, and R is an aryl or alkyl having from 1 to 10 carbon atoms. The invention further comprises methods for forming such compounds and for their use in preparing water soluble silane compositions by reaction with relative insoluble silane compounds terminated in functional groups selected from the group comprising epoxies, vinyls, mercaptos and acrylates.

23 Claims, No Drawings

PREPARATION AND USE OF ALKYLENEOXYSILANE COMPOSITIONS

FIELD OF THE INVENTION

The present invention relates to alkyleneoxysilanes, and more particularly to fully or partially hydrolyzed alkyleneoxysilanes and their preparation and use, for example, as silane solubilizing agents.

BACKGROUND OF THE INVENTION

Silane compounds have a wide variety of uses. It is often desirable to prepare an aqueous solution or a water-based composition of such silane compounds. Water soluble compositions of silanes are useful as primers for various metal substrates, additives in filler pretreatments, as aqueous resin systems, as an additive in binders, adhesives, sealants, surface coatings and paints (latex-acrylic).

Many otherwise useful silane compounds are, however, water insoluble. It is known to use silane-based compositions for solubilizing water-insoluble silanes. For example U.S. Pat. No. 5,051,129 issued Sep. 24, 1991, discloses the use of a coupling agent of the general formulae $A_{(4-n)} Si Y_n$, where A is a monovalent organic radical and Y is a hydrolyzable radical, and n is 1, 2 or 3. It is well known that certain silanes can be made water-soluble by, for example, pH adjustment. However, these solutions have limited stability, or shelf life, and contain by-product alcohols which are flammable. These prior art compositions have the disadvantages of employing flammable organic compounds as carriers or release volatile organic compounds ("VOC") as the silanes cure by hydrolysis.

It is therefore desirable to provide an inexpensive and convenient to use silane-based composition and method for solubilizing insoluble silanes that avoids the problems and limitations of the prior art. The invention also contemplates the water soluble, functionally-terminated silane end products that are essentially alcohol free (i.e., less than about 2% alcohol) and that they have a wide variety of industrial and commercial applications.

SUMMARY OF THE INVENTION

The need for an improved silane solubilizing composition is met by the present invention, which is directed to compositions comprising the fully or partially hydrolyzed alkyleneoxysilanes (Ia) and (IIa) shown below, and to their preparation and use.

Wherein R is an alkyl or aryl group having from 1 to 10 carbon atoms, b ranges from 1 to 30, x ranges from 1 to 3, y is 0 or 1, and z ranges from 1 to 3.

The hydrolyzed alkyleneoxysilanes of the present invention can be formed by dissolving alkyleneoxysilanes (I) or (II) in water followed by removal of the alcohol formed.

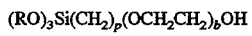

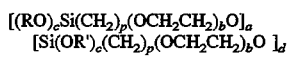

wherein, for both structures (I) and (II), p ranges from 2 to 10 with 3 preferred, b ranges from 1 to 30, R and R' represent the same or different hydrocarbons having from 1 to 10 carbon atoms, preferably 1 or 2, or $(CH_2CH_2O)_b(CH_2)_pSi(OR")_3$ wherein R" is a hydrocarbon having up to 10 carbon atoms and b and p are as defined with respect to (I) and (II). In structure (II), e ranges from 0 to 2, c ranges from 0 to 2, and a and d vary depending on the length or size of the oligomer or polymer.

DETAILED DESCRIPTION OF THE INVENTION

Alkyleneoxysilanes are a class of compounds in which the silicon is bound to the functional portion of the molecule by a silicon-carbon linkage and by a silicon-oxygen linkage.

The compounds of the present invention comprise the hydrolyzed alkyleneoxysilanes (Ia) and (IIa) shown below:

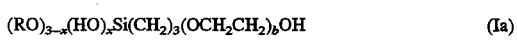

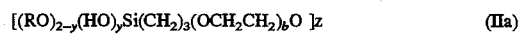

wherein R is an aryl or alkyl group having from 1 to 10 carbon atoms, b ranges from 1 to 30, x ranges from 1 to 3, y is 0 or 1, and z ranges from 1 to 3. Preferably, b ranges from 4 to 20, and most preferably from 4–10. As used herein, the term "hydrolyzed" means partially or completely hydrolyzed.

As previously noted, the hydrolyzed alkyleneoxysilanes of the present invention are useful for solubilizing water-insoluble silanes. The hydrolyzed alkyleneoxysilanes of the present invention can be formed by dissolving alkyleneoxysilanes having structures (I) or (II) in water followed by removal of the alcohol formed:

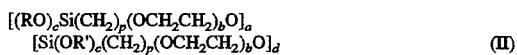

wherein, for both structures (I) and (II), p ranges from 2 to 10 with 3 preferred, b ranges from 1 to 30, R and R' represent a hydrocarbon having from 1 to 10 carbon atoms, preferably 1 or 2, or $(CH_2CH_2O)_b(CH_2)_pSi(OR")_3$ wherein R" is a hydrocarbon having up to 10 carbon atoms and b and p are as defined with respect to (I) and (II). In structure (II), e ranges from 0 to 2, c ranges from 0 to 2, and a and d vary depending on the length or size of the oligomer or polymer.

The structure (I) is further illustrated below:

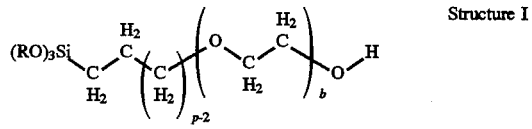

Structure I wherein p and b are as defined above.

The structure of compounds comprising formula (II) can be further illustrated by the structure (II)':

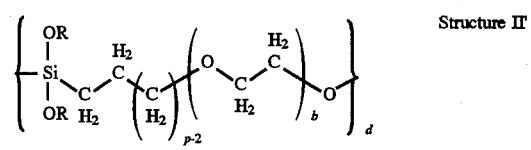

Structure II

Structure (II)' includes both linear and cyclic compounds. In structure (II)', R can be a $(CH_2CH_2O)_b(CH_2)_pSi(OR)_3$ group to provide a branched structure. A cyclic structure can be illustrated as follows:

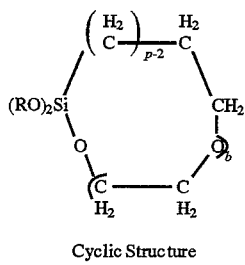

Cyclic Structure

Structures (Ia) and (IIa) can be written as structures (I) and (II) except with R and R' selected from the group consisting of a hydrocarbon having from 1 to 10 carbon atoms, $(CH_2CH_2O)_b(CH_2)_pSi(OR'')_3$ or H. Such compounds are formed in the presence of water, (where R and R' equal H), where condensation occurs to give siloxane linkages (SiOSi), in addition to other possibilities. An example of a siloxane structure can be illustrated as follows:

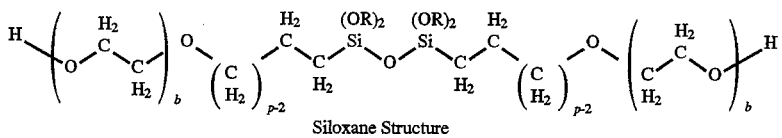

Siloxane Structure

The foregoing illustrations of structures (I), (II), (Ia), and (IIa) are intended to provide representative examples, but are not intended to be in any way limiting. Other possibilities will be evident to those skilled in the art.

The alkyleneoxysilanes (I) and (II) can be prepared in either a "one pot", two-step or a one pot, three-step procedure. In either the two-step or three-step procedure, a starting material is alkyleneoxy polyethylene glycol [PEG] which can be prepared or purchased commercially. As used herein, alkyleneoxy PEG, includes monoterminated alkyleneoxy polyethylene glycols, the preparation of which is known to those skilled in the art. Alkyleneoxy PEG compounds useful in accordance with the present invention can be illustrated as follows:

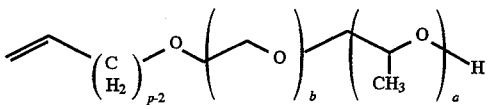

wherein p=2 to 10 with 3 preferred; a=0–30; b=0–30; a+b=1–30

The alkyleneoxy PEG starting material can be treated prior to hydrosilation with an agent to remove water and impurities which can interfere with the hydrosilation catalyst. For example, the alkyleneoxy PEG can be treated with Amberlyst-15® (a sulfonic acid cation exchange resin sold by the Rohm & Haas company) which effectively removes impurities that can interfere with a platinum hydrosilation catalyst. Other materials and procedures for treating the starting material will be apparent to those of ordinary skill in the art. For example, other cation exchange resins can be used. The pre-treatment required will depend on the quality of, and impurities present in, the alkyleneoxy PEG starting material.

The two-step process of preparing the alkyleneoxysilanes (I) and (II) is illustrated by equations (A) and (B):

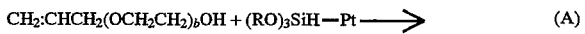  (A)

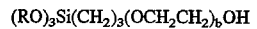

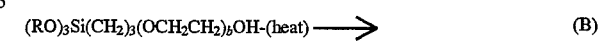  (B)

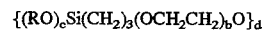

wherein R, b, c and d are defined as in formulas (I) and (II). In step (A) the alkyleneoxy PEG starting material is reacted with the trialkoxysilane in the presence of a hydrosilation catalyst, such as a platinum catalyst, to give the product of step (A). Suitable platinum catalysts include, but are not limited to, platinum 1,3-divinyltetramethyldisiloxane catalyst, referred to as the Karstedt catalyst, which is made and sold by Hüls America Inc. Other catalysts can also be used, for example, as described in Marciniec, B., *Comprehensive Handbook on Hydrosilylation* (Pergamon Press, 1992), the disclosure of which is herein incorporated by reference.

Following step (A), the resulting composition is heated, as in step (B), to remove unreacted starting materials. Also in step (B) a variable amount of alcohol is removed, resulting in condensation to longer chains, cyclics, or branched structures. The resulting product (structure (II)) is an oligomeric or polymeric composition which includes chains of indeterminant length. This can be converted to a purely polymeric composition by treatment with a suitable transesterification catalyst such as butyl titanate monomer. The polymeric composition occurs when d is greater than 2.

The three-step procedure for making the compounds (I) and (II) is shown by equations (C)–(E):

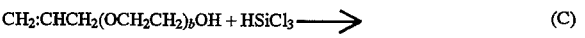  (C)

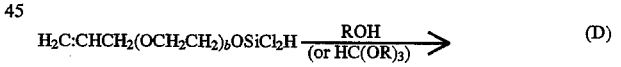  (D)

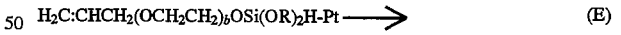  (E)

In the first step (C), the alkoxylation of trichlorosilane with the alkyleneoxy PEG results in a slightly exothermic liberation of hydrogen chloride gas. This step can be performed in the presence of a solvent, such as aliphatic or aromatic hydrocarbon, (e.g., heptane or toluene), or a chlorocarbon (e.g., 1,1,1-trichloroethane). Acceptable results are obtained when the trichlorosilane is dissolved in a solvent such as heptane and the alkyleneoxy PEG is added to the reaction mixture at a temperature greater than 50° C. The reaction can be run at between 50° C. and reflux. Alternatively, the alkyleneoxy PEG can first be dissolved in the solvent followed by the addition of trichlorosilane. The reaction can also be run in the absence of solvent but the removal of the liberated hydrochloric acid is more difficult, requiring reduced pressure, and a loss of Si-H as hydrogen is observed.

The esterification of the product of (C) can be carried out with alcohol, preferably in a solvent such as heptane, or with an orthoester as is shown in (D). It is important that essentially all of the HCl is removed during this step. The last traces of HCl can be removed with an orthoester or by reaction with an epoxide such as propylene oxide.

Alcohol can be used to dissolve the oligomeric/polymeric products of eqns. (C)–(E). The hydrosilation step shown in (E) can be carried out with an appropriate catalyst system, which leads to a taffy-like oligomeric/polymeric product which can be dissolved in alcohol at reflux. When the hydrosilation of (E) is performed in the presence of alcohol (0.1–0.9 equivalents preferred) the resulting product is a fluid having a lower viscosity. Those skilled in the art will understand that other reaction sequences can be used to obtain the final product of reaction (E).

The hydrolyzed alkyleneoxysilanes of the present invention can be formed using the alkyleneoxysilane products of reaction schemes (A), (B) or (E). As previously noted, such hydrolyzed alkyleneoxysilanes are suitable for solubilizing a silane which is water insoluble or has limited solubility in water. The hydrolyzed alkyleneoxysilanes are prepared by dissolving the composition resulting from reactions (A) and (B) or (E) in water, preferably deionized or distilled water, to effect hydrolysis. The hydrolysis is generally completed at ambient temperatures in about one hour and results in a stable, clear solution. In those cases where a slight haze is produced, the haze is readily removed by simple filtration.

During the hydrolysis, certain additional reactions can occur, including displacement of alcohol by water to generate silanol (see (F), below) and condensation to generate disiloxane (see (G), below).

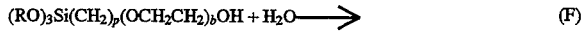

(F)

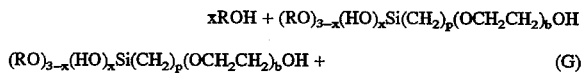

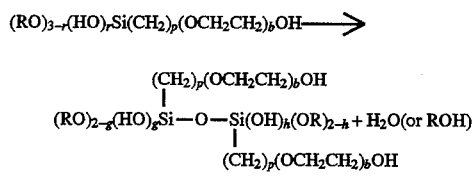

wherein g ranges from 0 to 2, h ranges from 0 to 2, r and x each range from 0 to 3, p ranges from 2 to 10, and b ranges from 0 to 30.

The solubilizing composition comprising hydrolyzed alkyleneoxysilanes can be used to solubilize a second, relatively insoluble silane. This is accomplished by adding the second, relatively insoluble silane directly to the hydrolyzed alkyleneoxysilane composition, and then allowing the reaction mixture to equilibrate. The alcohol that is generated is removed and replaced with an equal weight of water to provide the final composition.

The compounds and compositions of the invention are essentially alcohol-free, i.e., they contain less than about 2% alcohol. These materials have a very low VOC and low flashpoint.

Insoluble silanes that can be rendered water soluble in accordance with this method include, but are not limited to, the following classes of functionally-terminated compounds:

glycidoxypropyltrimethoxysilane,
glycidoxypropyltriethoxysilane,
3-methacryloxypropyltrimethoxysilane,
3-mercaptopropyltrimethoxysilane,
vinyltrimethoxysilane,
vinyltriethoxysilane, propyltrimethoxysilane,
methyltriethoxysilane and ethyltriethoxysilane.

Insoluble silanes that can be rendered water soluble in accordance with this method contain a hydrolyzable functionality, as illustrated by formula (H):

(H)

wherein $R^1$ and $R^2$ represent the same or different alkyl or functional alkyl groups having up to 8 carbon atoms, f ranges from 1 to 3, g ranges from 0 to 2, and f+g equals from 1 to 3. X represents any leaving group that will be known to those skilled in the art, including, but not limited to, OR (wherein R is an alkyl group having from 1 to 20 carbon atoms, with 1 and 2 preferred), $O_2CCH_3$, Cl, Br, I, NHR' or $NR'_2$ (wherein R' is an alkyl or aryl group having from 1 to 10 carbon atoms with 1 and 2 preferred). The exact mechanism of solubilization is not known with certainty; however, it is believed to occur through siloxane linkages between the insoluble silane and the soluble silane. It is believed that solubilization is promoted by the solubility of the polyethylene glycol portion of the molecule, which acts as a carrier.

Solubility studies have been conducted on alkyleneoxysilanes containing 0.5, 1.0, 7.2, and 10 EO units at 10 and 50 wt. % concentrations in deionized water. The 7.2 and 10 EO materials are immediately soluble in water. The lower molecular weight samples required from 2–48 hours with stirring to obtain sufficient hydrolysis and to effect solution. It is believed that solution initiates hydrolysis of the material to give carbinol-terminated silane species.

Functional silane solutions containing vinyl-, epoxy-, mercapto- and acrylate-terminated compounds produced in accordance with the invention exhibit long-term stability in an aqueous medium. These solutions also provide enhanced reactivity. As a group, these water soluble silanes find utility as safer and more environmentally acceptable replacements for related compounds that were previously available only in volatile organic solvent-based solutions.

Water soluble silanes produced in accordance with the invention and having the specified functional groups have a wide variety of uses in commercial and industrial applications.

Silanes with these functionalities are commonly used as coupling agents in systems containing the following resins:

1. Oligomeric vinyl functional silane solutions: Additive in filler pretreatments, fiberglass sizing and aqueous-based resins; use as a primer on metal substrates. Resin systems include:

Thermosetting—methyl methacrylate, paralene, polyimide.

Thermoplastic—PEK, PEEK, polyacrylate, polycarbonate, polyethylene, PVA, polyvinylbutyrol Sealants—acrylics, polysulfides, SBR Rubbers—silicone 2. Epoxy functional silane solutions: Additive in binders, urethanes, paints (latex-acrylic) and epoxy sealants; use as primer on metal substrates. Resin systems include:

Thermosetting—epoxy, melamine, phenolic, urethane.

Thermoplastic—polystyrene

Sealants—acrylic

Rubbers—butyl

Polymers—cellulosic, heparin, PVA, polysaccharides.

3. Oligomeric mercapto functional silane solutions: Additive in filler pretreatments of particulate minerals in vulcanized rubber; use as a primer on precious metal substrates. Resin systems include:

Thermosetting—epoxy, phenolic
Thermoplastic—polyacetal, polyphenylene-sulfide
Sealants—polysulfides
Rubbers—neoprene, isoprene, epichlorohydrin 4. Oligomeric methacrylate functional silane solutions: Additive in filler pretreatments, fiberglass sizing, aqueous-based resin systems; use as a primer on metal substrates. Resin systems include:

Thermosetting acrylics, polyester
Thermoplastic—polyacrylate
Sealants—acrylic

Preparation of Alkyleneoxysilanes

Non-limiting Examples 1–6 below illustrate the preparation of alkyleneoxysilanes that are suitable for use in the present invention and non-limiting examples 7–10 illustrate the preparation of solubilizing compositions comprising hydrolyzed alkyleneoxysilanes. Subscripts are as defined above.

EXAMPLES

Example 1

Preparation of $\{(CH_2)_3(OCH_2CH_2)_{0.5}OSi(OCH_3)_2\}_d$

In the preparation of $CH_2{:}CHCH_2(OCH_2CH_2)_{0.5}OSiCl_2H$, a one-liter ("1-L"), 4-necked reactor was fitted with overhead stirring, pot thermometer, pressure equalizing addition funnel (250 mL capacity), Allihn condenser topped with a dry ice/acetone cooled Dewar condenser, and a subsurface coarse fritted gas dispersion tube connected to a dry nitrogen source. To the pot was charged $CH_2{:}CHCH_2(OCH_2CH_2)_{0.5}OH$ (205.5 g, 1.74 mol). Trichlorosilane (248.3 g, 185 mL, 1.83 mol) was charged to the addition funnel and added dropwise, with stirring, to the reactor at 22° C. The temperature rose to 57° C. maximum and gas was evolved. The mixture darkened due to the presence of dissolved HCl and the temperature fell to 36° C.

Heat was applied with an infrared heat lamp to maintain the pot temperature at about 50° C. until the addition of the trichlorosilane was complete (1 h). Nitrogen was introduced into the reactor via the subsurface feed until a mild reflux was observed from the dry ice/acetone condenser to purge the dissolved hydrochloric acid from the product. The mixture was analyzed by GC to determine the amount of unreacted trichlorosilane. The excess was removed prior to the next step of the reaction sequence by applying a slight vacuum to the reactor and stripping to a cold trap. The product was obtained in 98.6% yield (365.5 g).

In the preparation of $\{(CH_2)_3(OC_2H_2)_{0.5}OSiCl_2\}_d$, approx. 10 g of the alkyleneoxy, dichlorohydridosiloxy PEG (described above) was added to a 500 mL flask equipped with a magnetic stirrer, pot thermometer, pressure equalizing addition funnel (500 mL capacity), and a water cooled condenser. A platinum catalyst was added to the pot (in this case, 5% chloroplatinic acid (CPA) in isopropanol (IPA) 100 μL) and external heat was applied. The pot temperature rose rapidly once above 65° C. to above 90° C. The remainder of the alkyleneoxy, dichlorohydridosiloxy PEG (355.5 g, 1.717 mol total) was added over a period of 80 minutes during which time the temperature was maintained at between 105°–145° C. by adjusting the rate of addition and adding more catalyst solution (100 μL) when the temperature fell below 97° C. The mixture was heated and trichlorosilane (13.4 g, 10 mL, 0.10 mol) was added to react with any remaining olefin.

To a 500 mL flask containing the reaction mixture described above and equipped with a magnetic stirrer, pot thermometer, and a distillation head fitted with a head thermometer, was added trimethylorthoacetate (TMOA)(a total of 452.5 g, 479 mL, 3.77 mol; initially 432.5 g was added) over a period of 40 minutes. The temperature gradually rose from 34° C. to 70° C. with the evolution of methyl chloride. Methyl acetate (b.p. 57.5° C.) was distilled off to drive the reaction to a final pot temperature of 102° C. After the addition was complete, more volatiles (240.9 g) were distilled off to 105° C. head (143° C. pot). Chloride analysis of the residue indicated 21 ppm chloride so additional TMOA (20 g) was added to complete the alkoxylation. Volatiles (61.1 g) were again distilled off to provide the product, $\{(CH_2)_3(OCH_2CH_2)_{0.5}Si(OCH_3)_2\}_d$ (317.2 g; 90% yield).

Example 2

Preparation of $\{(CH_2)_3(OCH_2CH_2)_{1.0}OSi(OCH_3)_2\}_d$

In the preparation of $CH_2{:}CHCH_2(OCH_2CH_2)_{1.0}OSiCl_2H$, a 1-L, 4-necked reactor was fitted with overhead stirring, pot thermometer, pressure equalizing addition funnel (250 mL capacity), Allihn condenser topped with a dry ice/acetone cooled Dewar condenser, and a subsurface coarse fritted gas dispersion tube connected to a dry nitrogen source. $CH_2{:}CHCH_2(OCH_2CH_2)_{1.0}OH$ prepared from 1 equivalent ethylene oxide: 1 equivalent allyl alcohol (400 g; M.W. ca. 139–191 g/mol; 2.88–2.094 mol), was charged to the reactor. To the addition funnel was added trichlorosilane (303.9 g; 226.45 mL; 2.244 mol) which was then added dropwise to the alcohol; the temperature rose to 43° C. with heavy evolution of HCl gas. The addition was completed over 1.5 h. Excess trichlorosilane (20.28 g; 0.150 mol) was removed in vacuo along with the orange color to provide (576.6 g; 95% based on reacted $HSiCl_3$) alkyleneoxyethoxydichlorosilane.

In the preparation of $\{(CH_2)_3(OCH_2CH_2)_{1.0}OSiCl_2\}_d$, a 500-mL flask was equipped with a magnetic stirrer, pot thermometer, pressure equalizing addition funnel (500 mL capacity), and a water-cooled condenser, to which was added toluene (8.67 g; 10 mL) and 100 μL catalyst (5% CPA in IPA). Alkyleneoxyethoxydichlorosilane (200 g; 0.687 mol as estimated by GC analysis) was charged to the addition funnel and the pot was heated to 88° C. The addition was begun and an exotherm to 119° C. was observed. The pot temperature was maintained between 88° C. and 100° C. during the 1 h addition. The pot was held at about 90° C. for 0.5 h after the addition was complete and additional trichlorosilane (12.9 g; 9.61 mL; 0.95 mol) was added dropwise to react with any surviving olefin. An exotherm occurred to 98° C. which persisted through most of the addition. Excess trichlorosilane (6.31 g; 0.046 mol) was removed in vacuo to provide 203.0 g product as the residue. Based on a molecular weight average of 291 g/mol for the starting material, the consumption of $HSiCl_3$ indicates as much as 7% unreacted olefin present.

To a 500-mL flask equipped with a magnetic stirrer, pot thermometer, and a distillation head fitted with a head thermometer containing the reaction mixture described above (100 g; 0.696 mol Si-Cl) was added TMOA (104 g; 110 mL; 0.864 mol) dropwise at 53° C. Volatiles (74.9 g total; a mixture of methyl chloride, methyl acetate, and TMOA) were distilled off as before to 121° C. head (180° C. pot) temperature to give $\{(CH_2)_3(OCH_2CH_2)_{2.0}OSi(OCH_3)_2\}_d$ as residue (95.5 g, 98.5% yield).

Example 3

Preparation of $\{(CH_2)_3(OCH_2CH_2)_{7.2}OSi(OCH_3)_2\}_d$

In the preparation of $CH_2{:}CHCH_2(OCH_2CH_2)_{7.2}OSiCl_2H$, a 1-L, 4-necked reactor was fitted with overhead stirring, pot thermometer, pressure equalizing addition funnel (250 mL capacity), Allihn condenser topped with a dry ice/acetone cooled Dewar condenser, and a subsurface coarse fritted gas dispersion tube connected to a dry nitrogen source. To the pot was added $CH_2{:}CHCH_2(OCH_2CH_2)_{7.2}OH$ (300 g; 0.824 mol). Trichlorosilane (149.8 g; 112 mL; 1.11 mol) was added with stirring and a slow nitrogen purge was introduced through the dispersion tube. Heat (infrared heat lamp) was applied during the last of the addition. Excess trichlorosilane (38.16 g; 28.4 mL; 0.28 mol) was removed at 16° C with vacuum (2 mmHg) to give a cloudy straw-colored product.

In the preparation of $\{(CH_2)_3(OCH_2CH_2)_{7.2}OSiCl_2\}_d$, a 500-mL, 3-necked flask was fitted with a water cooled condenser, pot thermometer, pressure equalizing addition funnel (250 mL capacity), magnetic stirring, and a nitrogen bypass. The product of the previous reaction (149.2 g; 0.322 mol) was charged to the addition funnel and catalyst (100 µL 5% CPA/IPA) was added to the pot. A small amount (ca. 10 mL) of the silane was added to the pot, the mixture was heated to 100° C., and the remainder of the contents of the addition funnel was added over 20 min. The final pot temperature was 80° C., and heat was applied for 30 min after the addition was complete. IR analysis indicated that all of the Si-H (2230 cm$^{-1}$) had been consumed. More trichlorosilane (13.4 g; 10 mL; 0.10 mol) was added to react with any unreacted olefin and the excess (8.4 g; 63 mL; 0.062 mol) was removed in vacuo to provide 145 g (97%) crude product.

To a 500-mL flask equipped with a magnetic stirrer, pot thermometer, and a distillation head fitted with a head thermometer containing the reaction mixture described above (122 g; 0.264 mol; 0.528 mol Si-Cl based on the amount of trichlorosilane consumed in the previous reaction) was added TMOA (105.5 g; 111 mL; 0.878 mol) dropwise with heating. Volatiles (42.34 g containing 24% TMOA) were distilled off to 82° C. head temperature (125° C. pot temperature) to provide 138.6 g crude $\{(CH_2)_3(OCH_2CH_2)_{7.2}OSi(OCH_3)_2\}_d$ which was further reduced in vacuo to give 113.3 g product and unreacted TMOA (20.3 g volatiles containing 90% TMOA).

Example 4

Preparation of $\{(CH_2)_3(OCH_2CH_2)_{10.2}OSi(OCH_3)_2\}_d$

In the preparation of $CH_2{:}CHCH_2(OCH_2CH_2)_{10.2}OSiCl_2H$, a 1-L, 4-necked reactor was fitted with overhead stirring, pot thermometer, pressure equalizing addition funnel (250 mL capacity), Allihn condenser topped with a dry ice/acetone cooled Dewar condenser, and a subsurface coarse fritted gas dispersion tube connected to a dry nitrogen source. To the pot was added $CH_2{:}CHCH_2(OCH_2CH_2)_{10.2}OH$ (485.5 g; 1.358 mol; average molecular weight as determined by CgC analysis=357.3 g/mol) Trichlorosilane (209.0 g; 155.7 mL; 1.54 mol) was added with stirring and a slow nitrogen purge was introduced through the dispersion tube. Heat (IR lamp) was applied during the last of the addition. Excess trichlorosilane (49.3 g, 36.7 mL, 0.364 mol) was removed in vacuo.

To a 1-L, 4-necked flask equipped with overhead stirrer, water cooled reflux condenser, pot thermometer, and a 1-L, pressure-equalizing addition funnel was added ca. 15 mL of the alkyleneoxy, dichlorohydridosilylpropoxy PEG described above. The remainder (602 g total) was charged to the addition funnel. Catalyst (200 µL CPA/IPA) was added to the pot and heated to 100° C. and the addition was begun. Heat was applied as necessary throughout the addition to maintain a pot temperature of 90°–100° C. No yield of the viscous product, $\{(CH_2)_3(OCH_2CH_2)_{10.2}OSiCl_2\}_d$, was determined since the material was taken directly to the next product.

The water cooled condenser on the reactor described above was replaced with a distillation head, and TMOA (trimethylorthoacetate)(342.6 g; 363 mL; 2.85 mol) was added dropwise beginning at 35° C. The addition was complete in 1 h with a final pot temperature of 65° C. Volatiles were distilled off to a head temperature of 54° C (110.1 g containing 6.5% TMOA) and the remainder was removed in vacuo (106.7 g containing 41% TMOA; 40° C./full oil pump vacuum) to give the cloudy, yellow product. A portion of this product was subjected to vacuum filtration through diatomaceous earth to provide 378 g of clear $\{(CH_2)_3(OCH_2CH_2)_{10.2}OSi(OCH_3)_2\}_d$.

Example 5

Preparation of $\{(CH_2)_3(OCH_2CH_2)_{10}OSi(OCH_2CH_3)_2\}_d$

A 2-L, 3-necked Morton flask was fitted with a 1-L, pressure-equalizing addition funnel, overhead stirrer, and an Allihn condenser under an atmosphere of nitrogen. $CH_2{:}CHCH_2(OCH_2CH_2)_{10}OH$ (2.0 kg; AAE-10 supplied by Rhone-Poulenc) was treated by passing it through methanol washed, nitrogen dried Amberlyst-15® (81 g washed with 1.5 L methanol, purged for 20 minutes with nitrogen then dried further by application of vacuum and sufficient heat to maintain about 25° C.). Triethoxysilane was treated by the addition of sufficient propylene oxide to reduce the level of hydrolyzable chlorides to less than 5 ppm. A premix consisting of AAE-10 (888.3 g; 838 ml; 1.782 mol) and triethoxysilane (297 g; 339.5 ml; 1.808 mol) was charged to the addition funnel. About 150 ml of the premix was added to the pot and 0.5 ml of Karstedt catalyst was added at 22° C. The temperature rose to 39° C. over 20 minutes. The pot was warmed to 60° C. to give a gold color. The remainder of the premix was added over about 2 hours at about 58°–72° C. Additional catalyst (0.5 ml) was added about halfway through the addition. The evolution of some gas was observed after the second addition of catalyst. After removing volatiles by distilling to a pot temperature of 194° C. at atmospheric pressure and further removal of volatiles to 100° C. pot temperature at 2 mm Hg, crude product (1115.3 g; 94.7% yield) was obtained. Since the loss of one equivalent of ethanol—leading to a linear polymer—would result in 1095 g of product, the loss of ethanol was incomplete. In the reaction sequence, excess of the olefin is not desirable because it can isomerize to give an enol ether which can slowly decompose and liberate propionaldehyde.

The triethoxysilane can be pretreated with propylene oxide to reduce the chloride content which is a benefit when using a platinum catalyst. Other trialkoxysilanes, such as trimethoxysilane, can also be used, with the noted differences being in the rate of hydrolysis, the composition of the volatiles removed from the final formulation, and, possibly, the presence of small amounts in the final composition.

Example 6

Preparation of $\{(CH_2)_3(OCH_2CH_2)_{10}OSi(OCH_2CH_3)_2\}_d$

A 2-L, 3-necked Morton flask was fitted with a 1-L pressure equalizing addition funnel, overhead stirrer, and an Allihn condenser under an atmosphere of nitrogen. An inverted graduated cylinder was placed in a beaker full of water and a vent line running from the reactor was vented to fill the graduated cylinder with any gas that might be produced by the reaction. A second line was placed in the graduated cylinder to remove any gas from it by the application of vacuum as necessary to monitor the amount of gas released. $CH_2{:}CHCH_2(OCH_2CH_2)_{10}OH$ (AAE-10) was treated by passing it through methanol-washed, nitrogen-dried Amberlyst-15® as in Example 5. Triethoxysilane was treated with propylene oxide to reduce the level of hydrolyzable chlorides to less than 5 ppm. To the flask was charged triethoxysilane (972.2 g; 5.92 mol; 1111 ml). This was heated to 60° C. and Karstedt catalyst (1 mL; 18.3 mg Pt) was added. Gas evolution (210 cc) was observed as the colorless solution changed from clear to straw colored. The mixture was heated to 75° C. for about 40 minutes and analyzed by gas chromatography to determine if any redistribution of the triethoxysilane had occurred. It was observed that the close boiling impurities normally found in triethoxysilane were no longer present. AAE-10 (1014.4 g; 2.035 mol; ~956 mL) was charged to the addition funnel and added over a 2 h period. The temperature was maintained between 72° and 78° C. and gas evolution was observed (3.3 L total; ~0.147 mol; ~2.5% of the Si-H as $H_2$) primarily during the first half of the addition. The excess triethoxysilane and other volatile materials (629.25 g) were removed by distillation to a pot temperature of 100° C. under reduced pressure until a pressure of 0.5 mm Hg was obtained. The product was present as the pot residue (1339.5 g; 99.32% yield).

Preparation of Solubilizing Compositions

The following solubilizing compositions utilize the alkyleneoxysilanes described above. While the following examples each employ $\{(EtO)_cSi(CH_2)_3(OCH_2CH_2)_bO\}_d$, it is to be understood that the other alkyleneoxysilanes described for use as solubilizing silanes can also be employed.

Example 7

To a 1-L, 3-necked, round-bottomed flask with an overhead stirrer, thermometer and an addition funnel to charge materials, was added 108 g of $\{(EtO)_cSi(CH_2)_3(OCH_2CH_2)_bO\}_d$ and 200 g $H_2O$. The solution was agitated until hydrolysis was complete (minimum 1 h). To the reaction mixture was added 27 g vinyltrimethoxysilane. The mixture was stirred for a minimum of 1 hour to ensure complete hydrolysis. The pH was adjusted to 7 by the addition of $NaHCO_3$ and then the solution was vacuum stripped of alcohol at 60° C. The solution was then replenished with $H_2O$ to its original weight. The final product was cleaned by filtering through diatomaceous earth. The resulting composition had a specific gravity of 1.05–1.07 at 20° C., contained 30–34% solids (2 g heated at 105° C. for 1 h), and showed no change in physical and spectral (IR) properties when stored at 25° C. for more than 6 months.

Example 8

To a flask as described in the preceding example was charged 108 g $\{(EtO)_cSi(CH_2)_3(OCH_2CH_2)_bO\}_d$ and 200 g $H_2O$. The solution was agitated until hydrolysis was complete. To this solution was added 27 g of water-insoluble glycidoxypropyltrimethoxysilane with stirring to complete hydrolysis. The resulting composition was vacuum stripped of alcohol at 60° C. and then replenished with water to its original weight. The viscosity, specific gravity, percentage of solids, and stability of spectral and physical properties of the final composition were similar to those of the composition of the preceding example.

Example 9

A composition was prepared as described in the preceding example up to the point of adding the second silane. Instead of adding glycidoxypropyltrimethoxysilane, 27 g of water-insoluble mercaptopropyltrimethoxysilane was added and stirred to complete hydrolysis. The solution was vacuum stripped and replenished with water as described in the preceding examples, resulting in a final water soluble composition having properties similar to those of the preceding examples. The stability of the spectral and physical properties were similar to those of the composition described in Example 8.

Example 10

A composition was prepared as described in Example 7 except that the second water-insoluble silane comprised methacryloxypropyltrimethoxysilane which was added after adjusting to p 7.5–9 with sodium bicarbonate, and the reaction temperature was maintained at below 45° C. The final water soluble composition also had similar properties and showed similar stability in spectral and physical properties.

As will be apparent to one of ordinary skill in the art, the compositions and methods described above can be employed to combine hydrolyzed alkyleneoxysilanes with a wide variety of relatively insoluble silanes to produce water soluble, functionally terminated silane compositions.

What is claimed is:

1. Hydrolyzed essentially alcohol-free alkyleneoxysilanes selected from the group consisting of $(RO)_{3-x}(HO)_xSi(CH_2)_3(OCH_2CH_2)_bOH$ and $[(RO)_{2-y}(HO)_ySi(CH_2)_3(OCH_2CH_2)_bO]_z$, wherein R is an aryl or alkyl group having from 1 to 10 carbon atoms, x ranges from 1 to 3, y is 0 or 1, z ranges from 1 to 3 and b ranges from 1 to 30.

2. The hydrolyzed alkyleneoxysilanes of claim 1 wherein b ranges from 4 to 20.

3. The hydrolyzed alkyleneoxysilanes of claim 1 wherein b ranges from 4 to 10.

4. The hydrolyzed alkyleneoxysilanes of claim 1 wherein R is a methyl or ethyl group.

5. A method of forming a hydrolyzed essentially alcohol-free alkyleneoxysilane comprising the steps of:

(a) providing an alkyleneoxysilane selected from the group consisting of $(RO)_3Si(CH_2)_3(OCH_2CH_2)_bOH$, $[(RO)_cSi(CH_2)_3(OCH_2CH_2)_bO]_d$ and $[(CH_2)_3(OCH_2CH_2)_bOSi(OR)_2]_d$, wherein R is an aryl or an alkyl group having from 1 to 10 carbon atoms, b ranges from 1 to 30, c ranges from 0 to 2 and d varies depending on the length or size of the oligomer or polymer; and (b) dissolving the alkyleneoxysilane of step (a) in water.

6. The method of claim 5 wherein the step of providing an alkyleneoxysilane further comprises the steps of:

(i) mixing an alkyleneoxy polyethylene glycol with a trialkoxysilane to form a mixture; and (ii) combining the mixture with a hydrosilation catalyst.

7. The method of claim 6 wherein the hydrosilation catalyst comprises a platinum catalyst.

8. The method of claim 7 wherein the platinum catalyst is platinum 1,3-divinyltetramethyldisiloxane complex.

9. The method of claim 5 wherein the step of providing an alkyleneoxysilane further comprises the steps of:

(i) reacting an alkyleneoxy polyethylene glycol with a trialkoxysilane to form a first composition;

(ii) esterifying the first composition with an alcohol ROH or an orthoester $HC(OR)_3$, wherein R is an alkyl group having up to 3 carbon atoms, to form a second composition; and (iii) hydrosilating the second composition by combining the second composition with a hydrosilation catalyst.

10. The method of claim 9 which further comprises performing steps (i)–(iii) in the presence of a solvent.

11. The method of claim 9 wherein the hydrosilation catalyst comprises a platinum catalyst.

12. A method for increasing the solubility of a silane in an aqueous composition comprising the steps of:

(a) reacting a solubilizing composition selected from the group consisting of $(RO)_{3-x}(HO)_xSi(CH_2)_3(OCH_2CH_2)_bOH$ and $[(RO)_{2-y}HO)_ySi(CH_2)_3(OCH_2CH_2)_bO]_z$, wherein R is an aryl or alkyl group having from 1 to 10 carbon atoms, z ranges from 1 to 3, b ranges from 1 to 30, y is 0 or 1 and x ranges from 1 to 3, with a second silane compound that is relatively insoluble in water;

(b) removing alcohol generated by the reaction of step (a); and (c) adding water to the composition of step (b).

13. The method of claim 12 wherein step (b) further comprises vacuum stripping.

14. The method of claim 12 where the reaction is conducted in an aqueous solution.

15. The method of claim 12 where the pH of the reactants is adjusted to about 7.

16. The method of claim 12 which includes the further step of filtering the composition of step (c).

17. The method of claim 12 wherein R is methyl or ethyl.

18. The method of claim 12 wherein b is from 4 to 10.

19. The method of claim 12 where the second relatively water insoluble silane has the formula $R_f^1R_g^2SiX_{4-f+g}$ wherein $R^1$ and $R^2$ represent the same or different alkyl or functional alkyl groups having up to 8 carbon atoms, f is from 1 to 3, g is from 0 to 2, (f+g) is from 1 to 3, X is an OR group (wherein R is an alkyl group having from 1 to 20 carbon atoms), $O_2CCH_3$, Cl, Br, I, or a NHR' or $NR'_2$ group where in R' is an alkyl or aryl group having from 1 to 10 carbon atoms.

20. The method of claim 12 where the second silane terminates in a functional group selected from the group consisting of epoxies, vinyls, mercaptos and acrylates.

21. A water soluble silane composition comprising the reaction product of a hydrolyzed alkeneoxysilane selected from the group consisting of $(RO)_{3-x}(HO)_xSi(CH_2)_3(OCH_2CH_2)_bOH$ and $[(RO)_{2-y}(HO)_ySi(CH_2)_3(OCH_2CH_2)_bO]_z$, wherein R is an aryl or alkyl group having from 1 to 10 carbon atoms, z ranges from 1 to 3, b ranges from 1 to 30, y is 0 or 1 and x ranges from 1 to 3, with a second silane compound that is relatively insoluble in water.

22. The composition of claim 21 where the second silane compound terminates in a functional group selected from the group comprising epoxies, vinyls, mercaptos and acrylates.

23. The composition of claim 21 wherein the second silane compound is selected form the group consisting of glycidoxypropyltrimethoxysilane, glycidoxypropyltriethoxysilane, 3-methacryloxypropyltrimethoxysilane, 3-mercaptopropyltrimethoxysilane, vinyltrimethoxysilane, vinyltriethoxysilane, propyltrimethoxysilane, methyltriethoxysilane and ethyltriethoxysilane.

* * * * *